(12) United States Patent
Erickson et al.

(10) Patent No.: US 6,357,136 B1
(45) Date of Patent: Mar. 19, 2002

(54) SCANNING ACOUSTIC MICROSCOPE SYSTEM AND METHOD FOR HANDLING SMALL PARTS

(75) Inventors: Daniel M. Erickson, Schiller Park; Bryan P. Schackmuth, Bensenville, both of IL (US)

(73) Assignee: Sonoscan, Inc., Elk Grove Village, IL (US)

( * ) Notice: Subject to any disclaimer, the term of this patent is extended or adjusted under 35 U.S.C. 154(b) by 0 days.

(21) Appl. No.: 09/689,135

(22) Filed: Oct. 12, 2000

(51) Int. Cl.[7] .............................................. F26B 19/00
(52) U.S. Cl. .................................. 34/60; 73/618; 73/620
(58) Field of Search ........................... 73/618, 620, 606, 73/608, 642, 644, 628, 600, 601, 629, 621, 627, 633, 582, 592, 596, 598, 41.2, 41.3, 41.4, 45.5; 34/60, 211, 232, 233, 241, 85, 192, 195

(56) References Cited

U.S. PATENT DOCUMENTS

| | | | | |
|---|---|---|---|---|
| 3,737,573 A | * | 6/1973 | Kessler | 73/608 |
| 3,790,281 A | * | 2/1974 | Kessler et al. | 73/606 |
| 3,850,027 A | * | 11/1974 | Nakanishi et al. | 73/600 |
| 3,886,793 A | * | 6/1975 | Cramer et al. | 73/601 |
| 3,898,839 A | * | 8/1975 | White | 73/644 |
| 4,008,602 A | * | 2/1977 | Love | 73/620 |
| 4,012,951 A | * | 3/1977 | Kessler | 73/606 |
| 4,208,915 A | * | 6/1980 | Edwards | 73/620 |
| 4,332,016 A | * | 5/1982 | Bernsten | 73/642 |
| 4,518,992 A | * | 5/1985 | Kessler et al. | 73/606 |
| 5,077,695 A | * | 12/1991 | Khuri-Yakub et al. | 73/642 |
| 5,431,054 A | * | 7/1995 | Reeves et al. | 73/628 |
| 5,600,068 A | * | 2/1997 | Kessler et al. | 73/620 |
| 5,684,252 A | | 11/1997 | Kesser et al. | |

* cited by examiner

*Primary Examiner*—Teresa Walberg
*Assistant Examiner*—Fadi H. Dahbour
(74) *Attorney, Agent, or Firm*—John H. Coult

(57) ABSTRACT

An improved tray-scanning station for a tray-fed scanning acoustic microscope prevents the dislodging of small, loosely held parts from the trays by coupling fluid as the trays pass through an inspection station, or by the action of a dryer as the trays pass through a drying station.

13 Claims, 3 Drawing Sheets

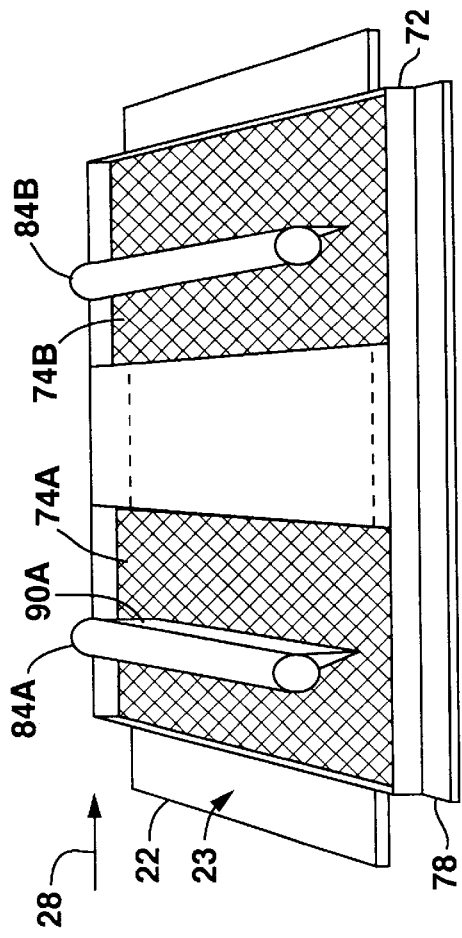
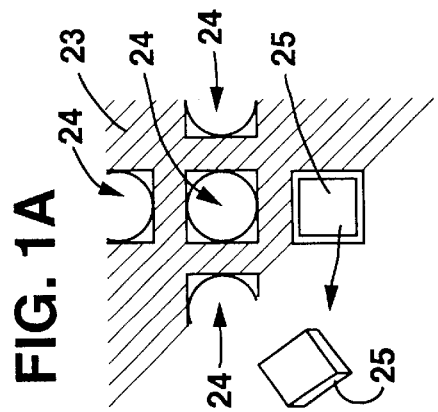
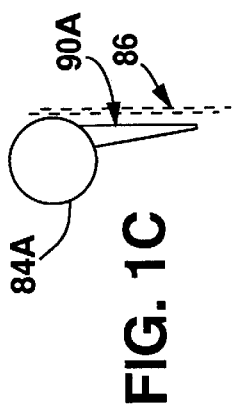
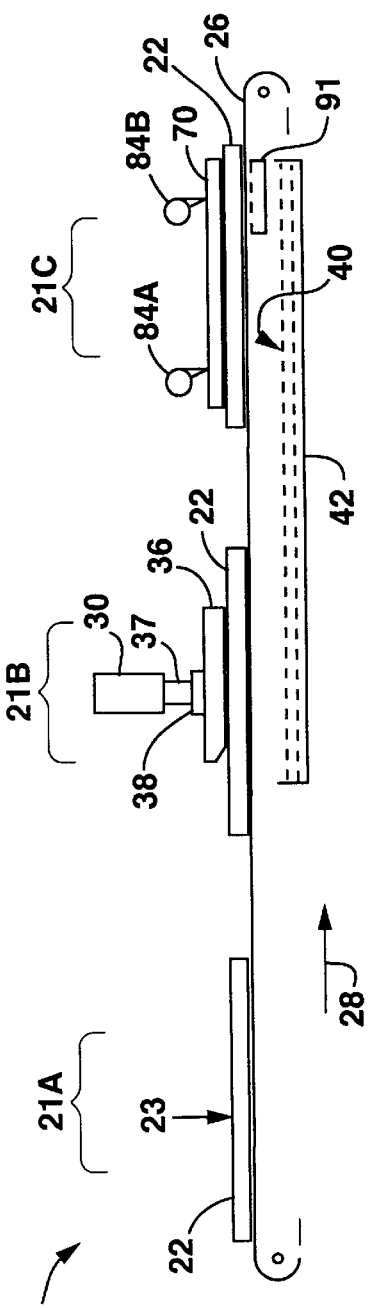
FIG. 1A
FIG. 1B
FIG. 1C
FIG. 1

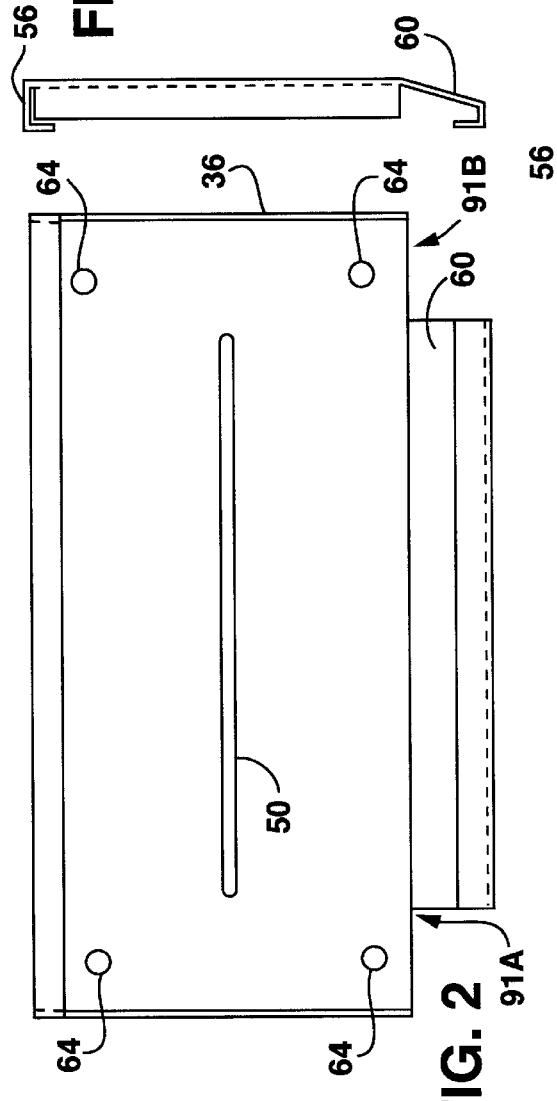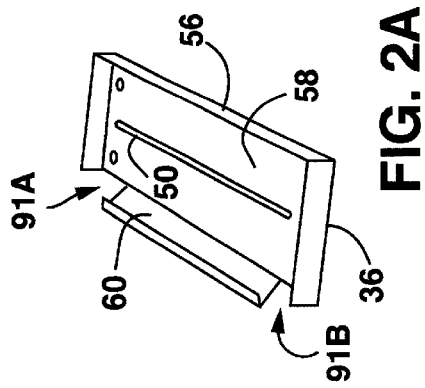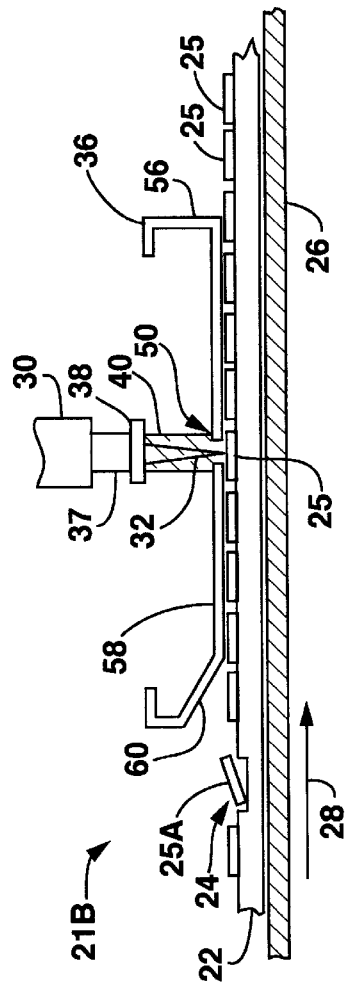

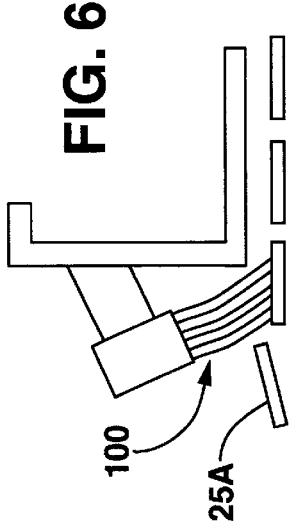
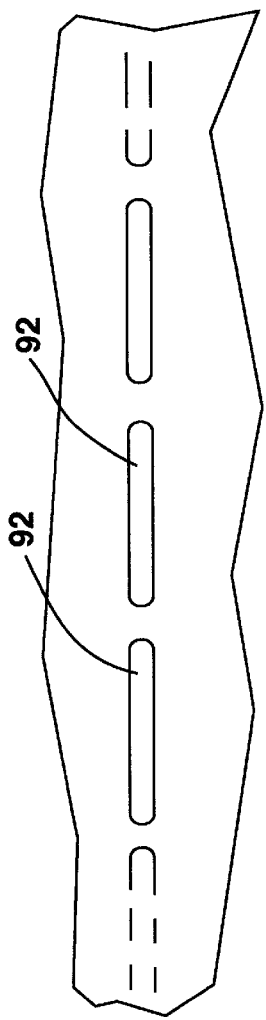
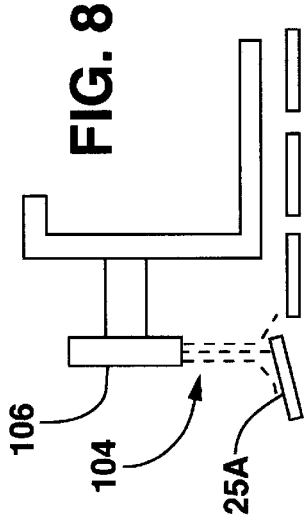
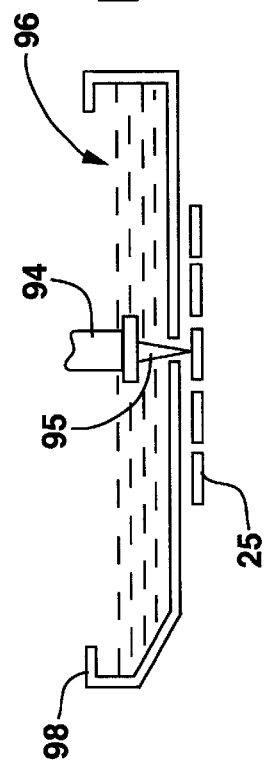
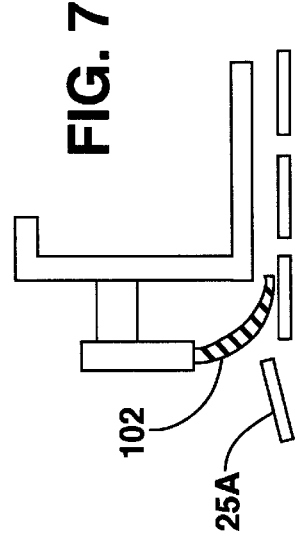

SCANNING ACOUSTIC MICROSCOPE SYSTEM AND METHOD FOR HANDLING SMALL PARTS

BACKGROUND OF THE INVENTION

This invention relates to scanning acoustic microscopes, commonly abbreviated "SAMs", used in the non-destructive testing of microcircuit parts, and is addressed specifically to a novel system for enhancing the capability of such systems in handling the parts under test.

A scanning acoustic microscope typically has an ultrasonic beam generator that is traversed rapidly back and forth over a part under test. To traverse the entire part, either the beam generator is scanned in two dimensions, or in one dimension, as the part is translated through the beam in the orthogonal dimension.

The image output of the scanning acoustic microscope is employed for the non-destructive analysis of the internal physical characteristics of the part. Operating at a very high frequency, the scanning acoustic microscope is able to penetrate through the part surface and image microscopic internal features in solids such as metals, ceramics, polymers, and composites. Typical components tested include microelectronic components such as integrated circuits (IC's), multi-layer ceramic capacitors, and multi-chip modules. Such components are commonly carried to the scanning station in trays known in the art as JEDEC trays. Faults typical of the parts tested include delaminations, cracks, tilts of discrete layers, disbonds, underfill coverage, and voiding.

It is a characteristic of high-frequency ultrasound that, while able to penetrate solids such as those described, high frequency ultrasound beams cannot pass through an air gap between the ultrasound beam generator and the part under test without severe attenuation. A fluid medium is therefore used to couple the high-frequency output of the scanning head of the ultrasonic beam generator to the part. The fluid medium is usually water, although alcohol and other fluids may be used. In one common approach, a coupling fluid is dispensed in a stream which embraces the ultrasonic beam.

It is the inevitable design trend in microelectronics that parts such as IC's are getting ever smaller. And as they diminish in size, the parts become more difficult to handle and manipulate, especially when tested in a production environment. In particular, a coupling fluid stream is very apt to agitate and dislodge such small parts from the trays as they move through the SAM.

U.S. Pat. No. 5,684,252 to Kessler et al, of common ownership herewith, shows a tray-fed SAM system in which trays of parts are each paired with an open mesh screen to hold the parts in the trays as they pass through the scanning station. The screens are removed from the trays after the scanning operation has been completed. This technique suffers from a requirement for a large number of screens of various sizes and configurations to accommodate different tray sizes and configurations. The screens represent an added capital and maintenance expense, and their handling a labor cost and delay.

OBJECTS OF THE INVENTION

It is an object of the invention to enhance the capability of a scanning acoustic microscope to acoustically inspect very small microelectronic ICs and other parts.

It is yet another object of the invention to provide an improved tray-scanning SAM station for handling trays of small, loosely held parts in a testing environment.

It is a more specific object of the invention to provide means and method for preventing the dislodgment of small parts from trays inspected in a SAM, or by a subsequent drying process.

It is an object of the invention to prevent dislodging of very small, loosely held parts from the trays by the turbulence in the coupling fluid dispensed by the scanning head in its traverse of the trays.

It is another object to provide means for re-nesting partially dislodged parts in the trays as they pass through a scanning station.

DESCRIPTION OF THE FIGURES

FIG. 1 is a schematic view in elevation of a multi-stage tray-fed scanning acoustic microscope apparatus embodying the invention; FIG. 1A is a detail view of the surface of a parts-holding tray passing through the apparatus of FIG. 1; FIG. 1B is a perspective view of a stationary parts-hold-down device used in a drying station, and FIG. 1C depicts operating details of a dryer element shown by FIG. 1B.

FIG. 2 is a plan view of a stationary parts-hold-down channel according to the invention; FIG. 2A is a perspective view of the channel, while FIGS. 2B and 2C show side and end views of the channel, respectively.

FIG. 3 is a cross-sectional view of the stationary parts-hold-down channel according to the invention.

FIG. 4 is a view of a section of a channel according to the invention, and depicting an alternate embodiment of a beam-passing slot.

FIG. 5 is a cross-sectional view of the channel showing an alternate embodiment of the channel depicted in FIG. 3.

FIGS. 6–8 depict alternate means for re-nesting partially dislodged parts in trays before they pass through the scanning station.

DESCRIPTION OF THE PREFERRED EXECUTION

The present invention is directed to a scanning acoustic microscope ("SAM") inspection system and method that enables the inspection of parts of such small size as to be incapable of being handled by prior art tray-fed SAM systems.

A preferred execution of the invention is illustrated in the Figures, in which like reference numerals in different Figures indicate like structure. The elements of the depicted execution will be first listed and identified with brief descriptive annotations where necessary to enlighten one skilled in the art, followed by a concise description of the operational method of the system. Finally, structure and method equivalents of the preferred execution will be described.

Structure of the Preferred Execution

REFERENCE NUMERAL DESCRIPTION

20—tray-fed scanning acoustic microscope
21A—station for loading trays of parts
21B—tray-scanning station
21C—drying station for drying trays of parts
22—tray for conveying the parts
23—surface of tray 22
24—pocket for receiving a part
25—a microelectronic part
25A—a part dislodged from its pocket
26—conveyor 28—direction of movement of conveyor 26 and trays 22
30—ultrasonic beam generator
32—ultrasonic beam
36—a parts-hold-down channel according to an aspect of the invention
37—transducer head
38—collar for dispensing coupling fluid
40—coupling fluid
42—reservoir
50—slot
56—a side of the channel
58—bottom pan
60—cant
64—holes for receiving hold-down screws
70—parts hold-down device according to an aspect of the invention
72—frame
74A, 74B—mesh
78—flange
84A—air knife
84B—air knife
86—streams of air
90A—plane of air knife 84A
91A, 91B—open sides of channel 36
92—slots
94—transducer head
95—ultrasonic beam
96—pool of coupling fluid
98—channel
100—brush
102—squeegee
104—stream of air
106—air nozzle A scanning acoustic microscope 20 shown in FIG. 1 comprises a station 21A for loading trays of parts (one tray 22 is shown), an improved tray-scanning station 21B for handling trays of small, loosely held parts, and an improved drying station 21C for drying trays of parts. A tray 22 holds parts as they are conveyed successively to the tray-scanning station 21B, and to the drying station 21C. The tray 22 may be of any of a variety of types and constructions such as a JEDEC tray—a standard in the industry, of which there are more than a hundred different configurations. As an example, the tray 22 used for exemplary purposes has a width dimension of 5.25; in. and a length dimension of 12.5 in.

With reference to FIG. 1A, surface 23 of tray 22 is shown as having of a plurality of pockets 24 for receiving ICs or other small parts, one of which is indicated at 25. In the JEDEC tray used as an example, there are 12 pockets width-wise and 29 pockets length-wise, for a total of 348 pockets. Each pocket 24 has the capacity for loosely holding a single microelectronic part that may be, by way of example, 0.22 in. square and 0.125 in. thick. The bottoms of the pockets 24 are open to allow a flow of coupling fluid around the loosely held parts and through the pockets 24.

A fluid-permeable conveyor 26, shown schematically in FIG. 1 as being a conventional belt conveyor, moves tray 22 to tray-scanning station 21B, then to drying station 21C. Tray-scanning station 21B has an ultrasonic beam generator 30 that emits an ultrasonic beam 32 (shown in FIG. 3) focused on the parts 25 carried by tray 22 as the tray 22 passes in the direction indicated by arrow 28. Ultrasonic beam generator 30 has a transducer head 37 for projecting an ultrasonic beam 32, and the transducer head 37 has a collar 38 for dispensing a coupling fluid 40 such as water coaxially with beam 32. Ultrasonic beam generator 30 moves transversely rapidly back and forth in its scanning function. The mechanism for driving ultrasonic beam generator back and fort_may be that described and claimed in U.S. Pat. No. 4,781,067 to Frank J. Cichanski, of common ownership herewith.

A stationary parts-hold-down channel 36 according to the invention is situated between the ultrasonic beam generator 30 and the trays 22 being conveyed through station 21B, and closely contiguous to the trays 22.

A means for capturing the coupling fluid 40 that drains through parts-hold-down channel 36 and conveyor 25, both described as being permeable to the coupling fluid 40, is shown as being a coupling fluid reservoir 42 located beneath scanning station 21B and drying station 21C.

The coupling fluid 40 dispensed from the collar 38 undesirably tends to dislodge parts 25 from the trays 22. Parts-hold-down channel 36 has at least one opening therein which is sized and positioned to pass a scanned ultrasound beam 32 from ultrasonic beam generator 30, but not to pass small parts 25 from the trays 22. The opening is indicated as being a slot 50 in this embodiment of the invention. The ultrasonic beam generator 30 is translated transverse to the path of tray 22, and the opening 50 is of sufficient width in the direction of tray movement to pass the coupling fluid 40 and the transversely moved ultrasound beam 32, but not to pass the small parts in the trays.

While stationary during operation, the channel 36 may be adjusted vertically between runs by means of an elevator structure (not shown) in order to accommodate trays of different heights. The elevator structure may be of conventional construction.

The ultrasonic beam generator 30 is depicted in FIG. 3 as focusing an ultrasound beam 32 through slot 50, where it will impinge on a succession of parts 25 in tray 22 in the tray's traverse through the scanning station 21B transverse to slot 50.

An attribute of the parts-hold-down channel 36 according to the invention is that trays 22 of small parts 25 are insonified without the parts being dislodged from the trays by coupling fluid as they traverse scanning station 21B.

With reference to FIG. 2–2C, the parts-hold-down channel 36 is depicted as having three closed sides, one of which is indicated at 56. Channel 36 has a bottom pan 58 that is slanted upwardly in the direction of approach of the conveyed trays 22 to form a fourth side having an upward cant 60. The purpose of the upward cant 60 according to the invention is to engage and re-nest dislodged parts (e.g., dislodged part 25A in FIG. 3) The upward cant 60 relative to bottom pan 58 can be an acute angle in the range of 10 to 30 degrees, and is preferably about 10 degrees.

By way of example, the parts-hold-down channel 36 according to the invention may have a length of about 8.25 in. and a width of about 3.75 in., with the upward cant section extending outwardly from the bottom pan 58 by about 0.69 in. The depth of the shallow sides may be about 0.44 in. The length of the slot may be bout 5.75 in, and its width about 0.093 in., all by way of example. Channel 36 may be composed of 0.032 stainless steel shim stock. It is noted that the bottom surface 58 of pan 60 must be unaffected by the machining of the slot and remain flat within about 0.01 in. to ensure the close contiguity of channel 36 and the tray 22 with its parts 25 passing beneath.

Channel 36 is held stationary by four machine screws (not shown), preferably of stainless steel. The four screws and inserted through the four holes 64, and threaded into a fixed part of the scanning acoustic microscope.

With reference to station 21C of FIG. 1, and to FIG. 1B, an improved drying station 21C according to the invention is shown which provides for drying trays of parts that have been insonified through a coupling fluid. Essentially, the drying station 21C comprises a dryer for removing coupling fluid, here shown as means for directing a stream or streams of forced gas onto wet trays of parts passing through the drying station.

However, the dryer undesirably agitates the parts and tends to dislodge them from the trays. A stationary parts hold-down device 70 is situated between the dryer and the trays and closely contiguous to the trays. The stationary hold-down device 70 is shown in this embodiment of the invention as comprising a frame 72 having a pattern of openings sized and positioned to pass streams of forced gas to the trays while precluding the small parts from escaping from the trays. The pattern of openings is indicated in this embodiment as comprising a two-section mesh 74A and 74B. The parts-hold-device 70 is made stationary by means of a flange 78 attached to a fixed part of the scanning acoustic microscope. An identical flange (not shown) is located on the opposite side of the frame 72.

While stationary during operation, like the channel 36 the hold-down device 70 may be adjusted vertically between runs by means of an elevator structure (not shown) in order to accommodate trays of different heights. The elevator structure may be of conventional construction.

Frame 72 is indicated as straddling a tray 22 of small, loosely held parts moving in the direction indicated by arrow 28. The parts placement on the surface 23 of tray 22 is depicted by FIG. 1A. The dryer in this embodiment is shown as comprising a pair of air knives 84A and 84B, indicated as being identical in construction. As depicted in FIG. 1C, air knife 84A develops a stream of air 86, depicted by the dash lines, along a plane 90A, producing a knife-like stream of air directed downwardly, in this example, toward the wet parts. Air knife 84B develops a similar stream of air. Moisture removal from the parts and trays may be enhanced by the provision of a vacuum dryer, shown schematically in FIG. 1 at 91.

The coupling fluid 40 that empties through slot 50 of channel 36, and the fluid that flows from the open sides 91A and 91B of the channel 36 (see FIG. 2A), as well as the coupling fluid 40 blown from parts 25 by the stream of forced gas from the air knives 84A and 84B of FIG. 1B, drains down through the tray 22 and the conveyor 26, and into the coupling fluid reservoir 42. From there, the coupling fluid may be filtered and recirculated to the fluid-dispensing collar 38 of the ultrasound beam generator 30.

Equivalents of the Preferred Execution

Other structures and methods that may be employed to implement the principles of the invention will now be described. Whereas a continuous uninterrupted slot 50 in channel 36 has been shown and described, the opening in channel 36 may take the form of a series of slots 92, as shown in FIG. 4. The slots 92 are sized and spaced to align with the parts passing beneath in such a way as to expose to the acoustic probe the parts, or specific areas of the parts, which are to be inspected.

With reference to FIG. 5, in ultra-high-resolution applications wherein the focal length of the beam is short, the transducer head 94 emitting an ultrasonic beam 95 may be submerged in the pool 96 of coupling fluid collected in the channel 98. An additional source of coupling fluid is metered into the channel 98 to control the desired depth of fluid.

Whereas the re-nesting of a dislodged part 25A is accomplished in the preferred embodiment by means of cant 60, re-nesting can be accomplished in other ways, such as by means of a soft brush 100 (FIG. 6), a squeegee 102 (FIG. 7), or a gentle air stream 104 produced by an air nozzle 106 (FIG. 8).

In the drying station, coupling fluid removal is accomplished in the preferred execution by means of a pair of gas jets. A single jet may be employed instead. The gas may be heated. The jet or jets may be pulsed or have their gas volume delivered according to a prescribed rate variation program. In addition to gas jets or in lieu of gas jets, or in combination with gas jets, the trays may be vibrated and/or have suction applied. Without the present invention to prevent dislodgement of the parts during the drying operation, these methods could not be employed, as they would surely cause parts to be dislodged from their holding trays.

While particular embodiments of the present invention have been shown and described, it will be obvious to those skilled in the art that changes and modifications may be made without departing from the invention in its broader aspects. Therefore, the appended claims are intended to cover all such changes and modifications as fall within the true spirit and cope of the invention. The matter set forth in the foregoing description and accompanying drawings is offered by way of illustration only and not as a limitation on the scope of the invention.

What is claimed is:

1. In a tray-fed scanning acoustic microscope, an improved tray-scanning station for handling trays of small, loosely held parts, comprising:

an ultrasonic beam generator;

a coupling fluid dispenser, the dispensed coupling fluid undesirably tending to dislodge the parts from the trays; and a stationary parts-hold-down channel situated between said ultrasonic beam generator and trays being conveyed through said station and closely contiguous to the trays, said device having at least one opening therein which is sized and positioned to pass an ultrasound beam from said ultrasonic beam generator, but not to pass the small parts from the trays, whereby the trays of small parts are insonified without the parts being dislodged from the trays by the coupling fluid as they traverse said scanning station.

2. The apparatus defined by claim 1 wherein said ultrasonic beam generator is translated transverse to the path of the trays and said opening is a transverse slot of sufficient width in the direction of tray movement to pass coupling fluid and said transversely moved ultrasound beam, but not to pass the small parts in the trays.

3. The apparatus defined by claim 1 which includes re-nesting means for re-nesting parts which have been partially dislodged from their holding trays.

4. The apparatus defined by claim 3 wherein said re-nesting means comprises a bottom pan on said channel having a surface which is canted upwardly in the direction of approach of the conveyed trays which engages and re-nests partially dislodged parts.

5. The apparatus defined by claim 1 wherein said channel has shallow sides to capture a volume of coupling fluid in the channel as the trays pass through said scanning station.

6. In a tray-fed scanning acoustic microscope for inspecting trays of small, loosely held parts, an improved drying station for drying trays of such parts which have been insonified through a coupling fluid, comprising:

a parts dryer, the dryer undesirably agitating the parts and tending to dislodge them from the trays; and a stationary parts-hold-down device situated closely contiguous to the trays, said hold-down device having a pattern of openings sized and positioned to preclude the small parts from being dislodged from the trays by the parts dryer as the trays move past the device.

7. In a tray-fed scanning acoustic microscope for inspecting trays of small, loosely held parts, an improved drying station for drying trays of such parts which have been insonified through a coupling fluid, comprising:

a parts dryer for directing a stream of forced gas onto wet trays of parts passing through the drying station, the forced gas undesirably agitating the parts and tending to dislodge them from the trays; and a stationary parts-hold-down device situated between said dryer and the trays and closely contiguous to the trays, said hold-down device having a pattern of openings sized and positioned to pass the stream of forced gas to the trays while precluding the small parts from being dislodged from the trays by the dryer as the trays move past the device.

8. In a tray-fed scanning acoustic microscope for inspecting trays of small, loosely held parts, the improvement comprising:

a scanning station, comprising:
an ultrasonic beam generator,
a coupling fluid dispenser, the dispensed coupling fluid undesirably tending to dislodge the parts from the trays, and
a stationary parts-hold-down channel situated between said ultrasonic beam generator and trays being conveyed through said scanning station and closely contiguous to the trays, said channel conducting coupling fluid from said dispenser to the trays of small parts through at least one opening therein which is sized and positioned to also pass an ultrasound beam from said ultrasonic beam generator but not to pass small parts from the trays, whereby the trays of small parts are insonified without the parts being dislodged from the trays by the coupling fluid as they traverse said scanning station; and a drying station for drying the trays of parts which have been insonified through a coupling fluid in said scanning station, comprising:

a parts dryer, the dryer undesirably agitating the parts and tending to dislodge them from the trays, and a stationary parts-hold-down device located closely contiguous to the trays, said hold-down device having a pattern of openings sized and positioned to preclude the small parts from being dislodged from the trays by the dryer as the trays move past the device.

9. The apparatus defined by claim 8 wherein said dryer develops at least one stream of forced gas.

10. The apparatus defined by claim 8 wherein said ultrasonic beam generator is translated transverse to the path of the trays and said opening is a transverse slot of sufficient width in the direction of tray movement to pass coupling fluid and said transversely moved ultrasound beam, but not to pass the small parts in the trays.

11. The apparatus defined by claim 10 wherein said hold-down channel has shallow sides to capture a volume of coupling fluid in the channel as the trays pass through said scanning station.

12. In a tray-fed scanning acoustic microscope, an improved tray-scanning station for handling trays of small, loosely held parts, comprising:

an ultrasonic beam generator;

a coupling fluid dispenser; and re-nesting means for re-nesting parts which have been partially dislodged from their holding trays before being scanned by an ultrasonic beam from the beam generator.

13. The apparatus defined by claim 12 wherein said re-nesting means comprises a parts hold-down channel situated between said beam generator and said trays, said channel having a bottom pan which includes a surface canted upwardly in the direction of approach of the conveyed trays which engages and re-nests partially dislodged parts.

* * * * *

UNITED STATES PATENT AND TRADEMARK OFFICE
CERTIFICATE OF CORRECTION

PATENT NO.    : 6,357,136 B1
DATED         : March 19, 2002
INVENTOR(S)   : Erickson et al.

It is certified that error appears in the above-identified patent and that said Letters Patent is hereby corrected as shown below:

Column 6,
Lines 31, 51 and 57, delete "channel", and substitute -- device --;

Column 8,
Line 28, before "re-nesting means", insert -- stationary --;
Line 34, delete "channel", and substitute -- device --; and
Lines 36-37, delete "the conveyed".

Signed and Sealed this

Twenty-second Day of July, 2003

JAMES E. ROGAN
*Director of the United States Patent and Trademark Office*